(12) United States Patent
Wentink et al.

(10) Patent No.: US 8,609,906 B2
(45) Date of Patent: Dec. 17, 2013

(54) PROCESS FOR PREPARING $C_1$-$C_4$-OXYGENATES BY PARTIAL OXIDATION OF HYDROCARBONS

(75) Inventors: Annebart Engbert Wentink, Mannheim (DE); Stefan Altwasser, Wachenheim (DE); Yan Li, Mannheim (DE); Michael Krämer, Mannheim (DE); Frank Rosowski, Mannheim (DE); Catharina Horstmann, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 280 days.

(21) Appl. No.: 12/967,337

(22) Filed: Dec. 14, 2010

(65) Prior Publication Data

US 2011/0144387 A1 Jun. 16, 2011

Related U.S. Application Data

(60) Provisional application No. 61/286,418, filed on Dec. 15, 2009.

(51) Int. Cl.
*C07C 27/00* (2006.01)

(52) U.S. Cl.
USPC ........................................................ 568/910

(58) Field of Classification Search
None
See application file for complete search history.

(56) References Cited

U.S. PATENT DOCUMENTS 5,763,678 A * 6/1998 Beckers et al. ............. 568/454
2009/0026415 A1* 1/2009 Parker et al. ............. 252/182.28

| | | |
|---|---|---|
| 2010/0069659 A1 | 3/2010 | Raichle et al. |
| 2010/0069660 A1 | 3/2010 | Raichle et al. |
| 2011/0028740 A1 | 2/2011 | Dobner et al. |
| 2011/0034707 A1 | 2/2011 | Wilmer et al. |
| 2011/0118487 A1 | 5/2011 | Abdallah et al. |
| 2011/0124885 A1 | 5/2011 | Altwasser et al. |

FOREIGN PATENT DOCUMENTS

WO WO-2005/037746 A1 4/2005
WO WO-2009/010407 A1 1/2009

OTHER PUBLICATIONS

K. Tabata et al., Catalysis Reviews 2002, vol. 44(1), pp. 1-58, especially pp. 1-25.
U.S. Appl. No. 13/021,242, Ewald et al.
U.S. Appl. No. 13/052,140, Altwasser et al.

* cited by examiner

*Primary Examiner* — Karl J Puttlitz
(74) *Attorney, Agent, or Firm* — Novak Druce Connolly Bove + Quigg LLP

(57) ABSTRACT

A process for preparing $C_1$-$C_4$-oxygenates from a reactant stream A which comprises essentially a $C_1$-$C_4$-alkane or a mixture of $C_1$-$C_4$-alkanes, by
a) branching off a substream B of the reactant stream A and allowing it to react in a reactor with oxygen or an oxygenous gas stream C, which converts a portion of the $C_1$-$C_4$-alkane or a portion of the mixture which comprises $C_1$-$C_4$-alkanes to $C_1$-$C_4$-oxygenates,
b) removing at least 90 mol % of the $C_1$-$C_4$-oxygenates formed from the product stream D resulting from step a) to form a remaining low boiler stream E, which comprises combining the low boiler stream E with the reactant stream A without further workup and without combination with the substream B down-stream of the branching site of the substream B.

17 Claims, 1 Drawing Sheet

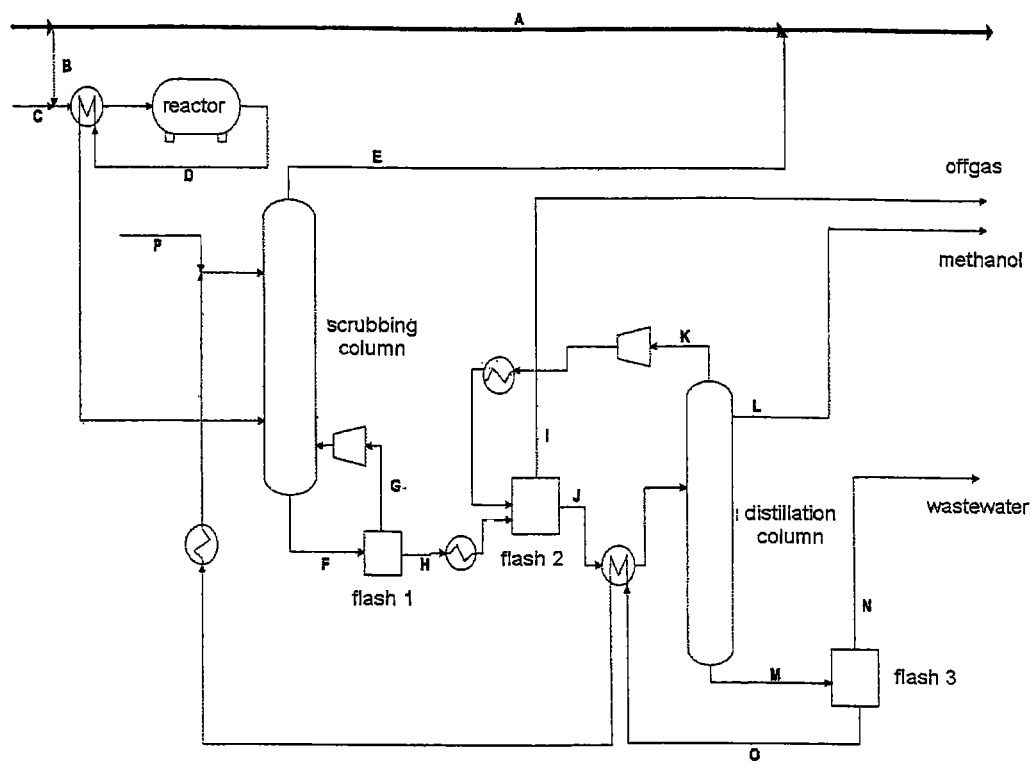

PROCESS FOR PREPARING C$_1$-C$_4$-OXYGENATES BY PARTIAL OXIDATION OF HYDROCARBONS

CROSS-REFERENCE TO RELATED APPLICATIONS

This Application claims the benefit of U.S. Provisional Application 61/286,418 filed on Dec. 15, 2009, the contents of which are incorporated herein by reference in its entirety.

FIELD OF THE INVENTION

The present invention relates to a process for preparing C$_1$-C$_4$-oxygenates from a reactant stream A which comprises essentially a C$_1$-C$_4$-alkane or a mixture of C$_1$-C$_4$-alkanes, by
a) branching off a substream B of the reactant stream A and allowing it to react in a reactor with oxygen or an oxygenous gas stream C, which converts a portion of the C$_1$-C$_4$-alkane or a portion of the mixture which comprises C$_1$-C$_4$-alkanes to C$_1$-C$_4$-oxygenates,
b) removing at least 90 mol % of the C$_1$-C$_4$-oxygenates formed from the product stream D resulting from step a) to form a remaining low boiler stream E,
which comprises combining the low boiler stream E with the reactant stream A without further workup and without combination with the substream B downstream of the branching site of the substream B.

BACKGROUND

C$_1$-C$_4$-Oxygenates, for example methanol, formaldehyde, acrolein, acrylic acid, are important products of the chemical industry.

Such C$_1$-C$_4$-oxygenates are typically not obtained on the industrial scale by direct partial oxidation of corresponding saturated hydrocarbons, but rather by an indirect route via intermediates. For example, C$_1$-oxygenates such as methanol or formaldehyde are obtained indirectly from methane. In this case, methane is first reacted with steam and oxygen to give synthesis gas, which is subsequently converted at relatively high pressures catalytically to methanol. The methanol can optionally be oxidized to formaldehyde in a further process.

A direct reaction of C$_1$-C$_4$-alkanes, preferably of methane, with oxygen or oxygenous gases to give the desired C$_1$-C$_4$-oxygenates would be much simpler and therefore highly attractive from an economic point of view.

The direct reaction of methane with oxygen or oxygenous gases to give C$_1$-oxygenates is of the greatest industrial interest according to the current state of knowledge. It is known and described in many scientific publications and in the patent literature, for example in K. Tabata et al., Catalysis Reviews 2002, volume 44(1), pages 1 to 58, especially pages 1 to 25. This reaction can be performed in the presence of catalysts or without catalysts.

In summary, however, the processes for preparing methanol from methane by direct partial oxidation of the methane, described in the prior art, have at least one of the following disadvantages:
a) in order to achieve a high methanol selectivity in the direct partial oxidation of methane to methanol, only a very small portion of a large amount of methane is converted to methanol; the unconverted amount of methane is recycled back into the oxidation reactor ("cycle gas process"). This is technically complex and not very economic since further process operations, such as compression, etc., firstly have to be carried out. Moreover, there may be enrichment of undesired secondary components or even undesired side reactions.
b) When the direct partial oxidation of methane to methanol is performed with high conversion of methane, the methanol selectivity is reduced, i.e. too high a level of undesired by-products form, which have to be removed again in a technically complex manner and hence impair the economic viability of such processes.
c) The use of aggressive or corrosive assistants, such as SO$_3$, NO$_x$ or halogen compounds, is technically complex.
d) Multistage reaction regimes require, inter alia, multiple reactors or reaction steps.

BRIEF SUMMARY

It was an object of the present invention to provide a process for preparing C$_1$-C$_4$-oxygenates by direct partial oxidation of C$_1$-C$_4$-alkanes, which does not have the disadvantages present in the prior art, and is especially notable for high selectivity of the conversion of C$_1$-C$_4$-alkane, for example methane, to the corresponding C$_1$-C$_4$-oxygenates, for example methanol and/or formaldehyde.

The object was achieved by the process defined in the claims.

BRIEF DESCRIPTION OF THE DRAWINGS

FIG. 1 shows a process flow diagram for one example of the process according to the invention.

DETAILED DESCRIPTION OF THE PREFERRED EMBODIMENTS

The reactant stream A comprises essentially a C$_1$-C$_4$-alkane or a mixture of C$_1$-C$_4$-alkanes, for example methane, ethane, propane, n-butane, isobutane or a two-component mixture or multicomponent mixture of these C$_1$-C$_4$-alkanes.

"Essentially" means herein that the reactant stream A comprises at least 80% by volume, preferably at least 90% by volume, of the C$_1$-C$_4$-alkane or of a mixture of C$_1$-C$_4$-alkanes.

Any remainder of the reactant stream A consists generally of nitrogen, hydrogen sulfide, carbon monoxide, carbon dioxide, water, other saturated or unsaturated hydrocarbons, noble gases, organic sulfur compounds and/or other impurities, in a total amount of typically in the range from 0 to 20% by volume, based on the reactant stream A.

In one embodiment, the reactant stream A comprises a mixture of C$_1$-C$_4$-alkanes.

The reactant stream A preferably comprises a mixture of C$_1$-C$_4$-alkanes which comprises a proportion of at least 70% by volume of methane, preferably of at least 80% by volume of methane, possibly in addition to ethane, propane, optionally butane and higher hydrocarbons.

The reactant stream A most preferably comprises essentially natural gas as an example of a mixture of C$_1$-C$_4$-alkanes.

The main component of natural gas is methane. A typical composition of natural gas is: 75 to 99% by volume of methane, 0.01 to 15% by volume of ethane, 0.01 to 10% by volume of propane, up to 0.06% by volume of butane and higher hydrocarbons, up to 0.30% by volume of carbon dioxide, up to 0.30% by volume of hydrogen sulfide, up to 0.15% by volume of nitrogen, up to 0.05% by volume of noble gas(es).

In a further embodiment, the reactant stream A comprises essentially methane or essentially propane; the reactant stream A most preferably comprises essentially methane.

Step a)

A substream B is branched off from the reactant stream A. According to the current state of knowledge, the amount of the substream B, based on the reactant stream A, is not critical. Typically, the substream B makes up 1 to 100% by volume, preferably 10 to 100% by volume and more preferably 20 to 60% by volume of the reactant stream A.

Before entry into a reactor or already within a reactor, the substream B is combined with oxygen or an oxygenous gas stream C and allowed to react in the reactor, which converts a portion of the $C_1$-$C_4$-alkane or a portion of the mixture which comprises $C_1$-$C_4$-alkanes to $C_1$-$C_4$-oxygenates.

Substream B and/or gas stream C can be heated before entry into the reactor, for example, as described below, by the product stream D, in a heat exchanger.

The molar ratio of the total amount of $C_1$-$C_4$-alkane (from the substream B): oxygen (from the gas stream C) is generally in the range from 99.9:0.1 to 75:25, preferably in the range from 99:1 to 90:10, more preferably in the range from 98:2 to 92:8.

The oxygenous gas stream C generally comprises oxygen in the range from 0.1 to 100% by volume, preferably in the range from 19 to 100% by volume. A very suitable oxygenous gas stream C is air.

The reaction of the substream B with oxygen or an oxygenous gas stream C can be effected in the form of a homogeneous gas phase reaction, in the form of a flame, in a burner or over a catalyst or a catalytically active surface, or in some other way.

According to the current state of knowledge, the nature of the reactor is uncritical. The term "reactor" should be understood in the present application to mean a reaction zone, which reaction zone may be represented, inter alia, by a reactor, a plurality of series-connected reactors or a cascaded reactor or a plurality of cascaded reactors. In numerical terms, reactor preferably means one reactor.

The reaction of the substream B with oxygen or an oxygenous gas stream C can in principle be carried out in all reactor types known from the prior art. Examples of very suitable reactors are described in Levenspiel, Octave; Chemical Reaction Engineering (3rd edition) John Wiley & Sons (1999).

The reaction of the substream B with oxygen or an oxygenous gas stream C in a reactor typically takes place within the temperature range from 40 to 900° C., preferably within the temperature range from 60 to 800° C., more preferably within the temperature range from 100 to 700° C., especially within the temperature range from 150 to 650° C., and at a pressure in the range from 1 to 200 bar, preferably in the range from 5 to 150 bar, more preferably in the range from 15 to 100 bar.

In the process according to the invention, a portion of the $C_1$-$C_4$-alkane or a portion of the mixture which comprises $C_1$-$C_4$-alkanes is converted to $C_1$-$C_4$-oxygenates. The corresponding conversion of the $C_1$-$C_4$-alkane or of a mixture of $C_1$-$C_4$-alkanes to the corresponding $C_1$-$C_4$-oxygenates is in the range from 0.1 to 10 mol %, preferably in the range from 1 to 8 mol %, more preferably in the range from 3 to 7 mol %.

In general, the selectivity of the inventive conversion of the $C_1$-$C_4$-alkane or of a mixture of $C_1$-$C_4$-alkanes to the corresponding $C_1$-$C_4$-oxygenates is high and is at least 70%, preferably in the range from 80 to 100%, more preferably in the range from 90 to 100%.

The reaction of the substream B with oxygen or an oxygenous gas stream C in a reactor can, apart from by supply of heat and/or pressure, also be influenced by performance of the reaction in the presence of a heterogeneous catalyst.

Such catalysts are known. The following groups are mentioned by way of example:

(i) supported or unsupported redox-active transition metal oxides or mixed oxides, for example based on iron, manganese, vanadium, molybdenum or copper, as described in the review article M. J. Brown and N. D. Parkyns: Catalysts Today 8 (1991) 305-335.

(ii) Supported transition metal complexes, for example platinum complexes, as described in WO 2005/037746.

Apart from those described above, the heterogeneous catalyst may also be a catalytically active surface, for example the inner surface of the reactor, as described, for example, in WO 2009/010407

For the inventive conversion of the $C_1$-$C_4$-alkane or of the mixture of $C_1$-$C_4$-alkanes to $C_1$-$C_4$-oxygenates in the presence of heterogeneous catalysts, the following reactors, which are known per se, are very suitable: fixed bed tubular or tube bundle reactor, fluidized bed reactor, tray reactor.

Step b)

The product stream D) resulting from step a) comprises, according to the composition of the substream B and the further reaction conditions, $C_1$-$C_4$-oxygenates, for example methanol and/or formaldehyde (methanal) as $C_1$-oxygenates, ethanol and/or acetaldehyde (ethanal) as $C_2$-oxygenates, n-propanol, isopropanol (2-propanol), acetaldehyde (propanal), acetone (dimethyl ketone), acrolein and acrylic acid as $C_3$-oxygenates, and n-butanol, n-butanal, isobutanol, maleic anhydride as $C_4$-oxygenates.

The product stream D typically has a temperature within the range from 40 to 800° C., preferably within the temperature range from 60 to 700° C., more preferably within the temperature range from 100 to 600° C., especially within the temperature range from 150 to 550° C.

The product stream D leaves the reactor and can be sent without further detours directly to the apparatus for removing the $C_1$-$C_4$-oxygenates.

In a preferred variant, however, the product stream D leaves the reactor and flows through a heat exchanger which is likewise entered by substream B and/or gas stream C, preferably in countercurrent, before they pass into the reactor. For instance, substream B and/or gas stream C are heated before they pass into the reactor.

Product stream D leaves the heat exchanger and generally passes without further detours to the apparatus for removing the $C_1$-$C_4$-oxygenates.

The $C_1$-$C_4$-oxygenates are removed to an extent of at least 90 mol %, generally virtually completely, from the product stream D by customary processes and the customary apparatus.

Such processes are, for example, absorption with a solvent ("scrubbing"), distillation, condensation, adsorption, membrane processes or a combination of these processes, for example distillation and condensation. Preference is given to absorption with a solvent ("scrubbing"). Preferred solvents for this purpose are the solvents in which the $C_1$-$C_4$-oxygenates have good solubility, for example water, $C_1$-$C_{10}$-alcohols having at least one OH group, such as glycols or polyglycols.

Suitable apparatus for the described removal of the $C_1$-$C_4$-oxygenates is, for example, absorption columns, adsorption columns, condensation vessels.

The removal apparatus, preferably the apparatus for absorption with a solvent or solvent mixture, may be connected in series or else alongside one another, in this case too optionally in series.

The separating processes described removed at least 90 mol % of the $C_1$-$C_4$-oxygenates formed in step a).

This results in a low boiler stream E and a high boiler stream F which comprises the $C_1$-$C_4$-oxygenates removed.

Typically, the product stream D is cooled by the employment of the separating processes described. However, the product stream D may also be cooled by customary methods already before entry into the apparatus for removal of the $C_1$-$C_4$-oxygenates.

The low boiler stream E comprises, in addition to $C_1$-$C_4$-alkanes unconverted in step a) and not removed thereafter, or a mixture of unconverted or unremoved $C_1$-$C_4$-alkanes, any carbon dioxide and carbon monoxide formed, and any substances already present in the reactant stream A, such as nitrogen, noble gas(es), carbon dioxide, carbon monoxide or further by-products formed, for example, in step a), and other impurities already present in reactant stream A.

The low boiler stream E preferably comprises a total amount of carbon dioxide in the range from 0 to 3% by volume, based on the low boiler stream E.

The low boiler stream E preferably comprises water in an amount in the range from 0 to 6% by volume, based on the low boiler stream E.

The low boiler stream E, without further workup and without combination with the substream B, is combined with the reactant stream A downstream of the branching site of the substream B. In this way, the low boiler stream E as such is not recycled back into the reactor. The process according to the invention thus works in "straight pass".

It is possible to isolate the $C_1$-$C_4$-oxygenates from the high boiler stream F by the customary separating processes as described above, i.e. to remove them from the further constituents of the high boiler stream F, for example "scrubbing liquid".

In a very suitable process, the high boiler stream F generally passes into one or more evaporators preferably connected in series (also referred to as "flash"), in which a lower pressure exists than in the upstream plant parts, for example reactor or separating apparatus, such as absorption column. Typically, the pressure in the first or sole evaporator is in the range from 5 to 30 bar, and in the second or any further evaporator typically 10 to 20 bar lower than in the upstream evaporator, but not below 0.1 bar.

The low boiler stream from the first evaporator G generally still comprises $C_1$-$C_4$-alkanes and is generally brought back to the pressure which exists in the apparatus for separation of the streams E and F, and fed into this apparatus.

The high boiler fraction from the first evaporator H is generally fed into the second evaporator and separated there into a low boiler stream I typically comprising $C_1$-$C_4$-alkanes, carbon dioxide, carbon monoxide, water and a low level of $C_1$-$C_4$-oxygenates, and a high boiler stream J comprising essentially the scrubbing liquid and the $C_1$-$C_4$-oxygenate. The low boiler stream I is typically disposed of as offgas, for example incinerated.

The high boiler stream J is generally fed into a separating apparatus, for example an apparatus for performing the abovementioned separating processes, preferably a distillation column, with which the $C_1$-$C_4$-oxygenates L are isolated from the further constituents of the high boiler stream J. The remaining residue M, essentially comprising the "scrubbing liquid" and water can, for example, be separated via an evaporator into the wastewater N and the scrubbing liquid O. The scrubbing liquid O can be fed together with fresh scrubbing liquid P back to the apparatus for separating the streams E and F.

FIG. 1 shows a process flow diagram for one example of the process according to the invention.

In a particularly preferred process according to the invention, which is described hereinafter, the reactant stream A is natural gas which flows through a customary pipeline. Useful natural gases are all natural gas types, for example those described above.

Step a)

A substream B is branched off from the natural gas stream A of the pipeline. According to the current state of knowledge, the amount of the substream B, based on the natural gas stream A, is not critical. Typically, the substream B makes up 1 to 100% by volume, preferably 10 to 100% by volume, more preferably 20 to 60% by volume, of the natural gas stream A.

The substream B is then, before entry into a reactor or already within a reactor, combined with oxygen or an oxygenous gas stream C and allowed to react in the reactor, which converts a portion of the natural gas to methanol and/or formaldehyde, preferably methanol.

Substream B and/or gas stream C can be heated before entry into a reactor, for example, as described below, by the product stream D in a heat exchanger.

The molar ratio of the total amount of $C_1$-$C_4$-alkane (from substream B): oxygen (from gas stream C) is generally in the range from 99.9:0.1 to 75:25, preferably in the range from 99:1 to 90:10, more preferably in the range from 98:2 to 92:8.

The oxygenous gas stream C generally comprises oxygen in the range from 0.1 to 100% by volume, preferably in the range from 19 to 100% by volume. A suitable oxygenous gas stream C is air.

The reaction of the substream B with oxygen or an oxygenous gas stream C can be effected in the form of a homogenous gas phase reaction, in the form of a flame, in a burner or over a catalyst, or in some other way.

According to the current state of knowledge, the nature of the reactor is uncritical. The term "reactor" should be understood in the present application to mean a reaction zone, which reaction zone may be represented, inter alia, by a reactor, a plurality of series-connected reactors or a cascaded reactor or a plurality of cascaded reactors. In numerical terms, reactor preferably means one reactor.

The reaction of the substream B with oxygen or an oxygenous gas stream C can in principle be carried out in all reactor types known from the prior art. Examples of very suitable reactors are described in Levenspiel, Octave; Chemical Reaction Engineering (3rd edition) John Wiley & Sons (1999).

The reaction of the substream B with oxygen or an oxygenous gas stream C in a reactor typically takes place within the temperature range from 40 to 900° C., preferably within the temperature range from 60 to 800° C., more preferably within the temperature range from 100 to 700° C., especially within the temperature range from 150 to 650° C., and at a pressure in the range from 1 to 200 bar, preferably in the range from 5 to 150 bar, more preferably in the range from 15 to 100 bar.

In the particularly preferred process, a portion of the natural gas is converted to methanol and/or formaldehyde, preferably methanol. The corresponding conversion of the natural gas to methanol and/or formaldehyde, preferably methanol, is in the range from 0.1 to 10 mol %, preferably in the range from 1 to 8 mol %, more preferably in the range from 3 to 7 mol %.

In general, the selectivity of the preferred conversion of the natural gas to methanol and/or formaldehyde, preferably methanol, is high and is at least 70%, preferably in the range from 80 to 100%, more preferably in the range from 90 to 100%.

The reaction of the substream B with oxygen or an oxygenous gas stream C in a reactor can, apart from by supply of heat and/or pressure, also be influenced by performance of the reaction in the presence of a heterogeneous catalyst.

Such catalysts are known. The following groups are mentioned by way of example:
(i) supported or unsupported redox-active transition metal oxides or mixed oxides, for example based on iron, manganese, vanadium, molybdenum or copper, as described in the review article M. J. Brown and N. D. Parkyns: Catalysis Today 8 (1991) 305-335
(ii) Supported transition metal complexes, for example platinum complexes, as described in WO 2005/037746.

Apart from those described above, the heterogeneous catalyst may also be a catalytically active surface, for example the inner surface of the reactor, as described, for example, in WO 2009/010407.

For the inventive conversion of the natural gas to methanol and/or formaldehyde, preferably methanol, in the presence of heterogeneous catalysts, the following reactors, which are known per se, are very suitable: fixed bed tubular or tube bundle reactor, fluidized bed reactor, tray reactor.

Step b)

The product stream D resulting from step a) comprises methanol and/or formaldehyde, preferably methanol, as essential constituents from the group of the $C_1$-$C_4$-oxygenates.

The product stream D typically has a temperature in the range from 40 to 800° C., preferably in the range from 60 to 700° C., more preferably in the range from 100 to 600° C., especially in the range from 150 to 500° C.

The product stream D leaves the reactor and can be sent without further detours directly to the apparatus for removing the methanol and/or formaldehyde, preferably methanol.

In a preferred variant, however, the product stream D leaves the reactor and flows through a heat exchanger which is likewise entered by substream B and/or gas stream C, preferably in countercurrent, before they pass into the reactor. For instance, substream B and/or gas stream C are heated before they pass into the reactor.

Product stream D leaves the heat exchanger and generally passes without further detours to the apparatus for removing the methanol and/or formaldehyde, preferably methanol.

The methanol and/or formaldehyde, preferably methanol is removed to an extent of at least 90 mol %, generally virtually completely, from the product stream D by customary processes and the customary apparatus.

Such processes are, for example, absorption with a solvent ("scrubbing"), distillation, condensation, adsorption, membrane processes or a combination of these processes, for example distillation and condensation. Preference is given to absorption with a solvent ("scrubbing"). Preferred solvents for this purpose are the solvents in which the methanol and/or formaldehyde have good solubility, for example water, $C_1$-$C_{10}$-alcohols having at least one OH group, such as glycols or polyglycols.

Suitable apparatus for the described removal of the methanol and/or formaldehyde, preferably methanol, is, for example, absorption columns, adsorption columns, condensation vessels.

The removal apparatus, preferably the apparatus for absorption with a solvent or solvent mixture, may be connected in series or else alongside one another, in this case too optionally in series.

The separating processes described removed at least 90 mol % of the methanol and/or formaldehyde, preferably methanol, formed in step a).

This results in a low boiler stream E and a high boiler stream F which comprises the methanol and/or formaldehyde, preferably methanol, removed.

Typically, the product stream D is cooled by the employment of the separating processes described. However, the product stream D may also be cooled by customary methods already before entry into the apparatus for removal of the methanol and/or formaldehyde, preferably methanol.

The low boiler stream E comprises, in addition to natural gas unconverted in step a) and not removed thereafter, any carbon dioxide and carbon monoxide formed, and any substances already present in the reactant stream A, such as nitrogen, noble gas(es), carbon dioxide, carbon monoxide or further by-products formed, for example, in step a), and other impurities already present in reactant stream A.

The low boiler stream E preferably comprises a total amount of carbon dioxide in the range from 0 to 3% by volume, based on the low boiler stream E.

The low boiler stream E preferably comprises water in an amount in the range from 0 to 6% by volume, based on the low boiler stream E.

The low boiler stream E, without further workup and without combination with the substream B, is combined with the reactant stream A downstream of the branching site of the substream B. In this way, the low boiler stream E as such is not recycled back into the reactor. The process according to the invention thus works in "straight pass".

It is possible to isolate the methanol and/or formaldehyde, preferably methanol, from the high boiler stream F by the customary separating processes as described above, i.e. to remove them from the further constituents of the high boiler stream F, for example "scrubbing liquid".

In a very suitable process, the high boiler stream F generally passes into one or more evaporators preferably connected in series (also referred to as "flash"), in which a lower pressure exists than in the upstream plant parts, for example reactor or separating apparatus, such as absorption column.

Typically, the pressure in the first or sole evaporator is in the range from 5 to 30 bar, and in the second or any further evaporator typically 10 to 20 bar lower than in the upstream evaporator, but not below 0.1 bar.

The low boiler stream from the first evaporator G generally still comprises $C_1$-$C_4$-alkanes and is generally brought back to the pressure which exists in the apparatus for separation of the streams E and F, and fed into this apparatus.

The high boiler fraction from the first evaporator H is generally fed into the second evaporator and separated there into a low boiler stream I typically comprising $C_1$-$C_4$-alkanes, carbon dioxide, carbon monoxide, water and a low level of $C_1$-$C_4$-oxygenates, and a high boiler stream J comprising essentially the scrubbing liquid and the methanol and/or formaldehyde, preferably methanol. The low boiler stream I is typically disposed of as offgas, for example incinerated.

The high boiler stream J is generally fed into a separating apparatus, for example an apparatus for performing the abovementioned separating processes, preferably a distillation column, with which the methanol and/or formaldehyde, preferably methanol, L are isolated from the further constituents of the high boiler stream J. The remaining residue M, essentially comprising the "scrubbing liquid" and water can, for example, be separated via an evaporator into the wastewater N and the scrubbing liquid O. The scrubbing liquid O can be fed together with fresh scrubbing liquid P back to the apparatus for separating the streams E and F.

FIG. 1 likewise shows a process flow diagram for one example of the preferred process.

EXAMPLE 1

The process according to the invention was simulated with the aid of the software ASPENplus for a stream B of virtually pure methane, a methane conversion of 5 mol %, an oxygen conversion of 100 mol %, a methanol selectivity of 90% (remainder to $CO_2$), an annual methanol capacity of 1 million tonnes, at a reactor temperature of 500° C. and a pressure of 50 bar.

Mass flows of 1394 t/h of methane and 90 t/h of oxygen were used.

The methanol was branched off directly from a pipeline (reactant stream A) at a pressure of 50 bar (for example immediately upstream of a compaction station).

The stream B and the stream C to the reactor were heated by the product stream D from the reactor to a temperature of 412° C., which cooled the product stream D to a temperature of 150° C. The total amount of heat exchanged corresponded to 462 MW. The heat of reaction released under the above-mentioned conditions was 237 MW. This heat is utilized partly (131 MVV) to preheat reactant streams B and C, and to raise steam (106 MW).

The product stream D was subsequently passed into a scrubbing column wherein the methanol formed was absorbed with the aid of a suitable solvent composed of 2.4% by weight of water in triethylene glycol.

The necessary mass flow of solvent was 1150 t/h. The temperature of the gas stream D was cooled there to approx. 41° C. The remaining gas stream E (approx. 1342 t/h) which, as well as 0.5 mol % of $CO_2$, comprised principally methane was recycled into the pipeline downstream of the branching site of the substream B without further workup and without combination with the substream B.

The methanol-laden solvent stream F was introduced into evaporator 1 and decompressed down to 18 bar. The resulting gas stream G was subsequently compressed back to 50 bar and recycled to the absorption column. Thereafter, the laden solvent stream H was heated with the aid of steam to a temperature of 110° C. and conducted at a pressure of 2.5 bar to the evaporator 2, where 2.2 t/h of offgas I were removed. The latter had the following composition: 93.7 mol % of methane, 2.5 mol % of carbon dioxide, 3.4 mol % of methanol and 0.4 mol % of water.

The resulting solvent stream J subsequently passes at 0.8 bar into a distillation column, where the desired methanol reaction product is isolated and the solvent is regenerated. The heat of evaporation needed for that purpose was 52.7 MW, the heat of condensation released 88.7 MW. In this manner, a total of 125 t/h of methanol were removed during the rectification.

In evaporator 3, at a pressure of 0.4 bar, 15.9 t/h of wastewater N, which consisted to an extent of 99.4 mol % of water, to an extent of 0.5 mol % of triethylene glycol and to an extent of 0.1 mol % of methanol, were removed from the solvent. The regenerated solvent O was circulated together with 680 kg/h of fresh solvent P.

The example described above gave a methane use number defined by the quotient=t(methane)/t(methanol) of 0.57 (and an oxygen use number of 0.72 [=t(oxygen)/t(methanol)].

The specific power consumption was 2.4 MW. This resulted in a steam credit (in the sense of steam raised or obtained) of 122.4 t/h, and a cooling water consumption of 4900 m³/h.

EXAMPLES 2 to 8

Examples 2 to 8 describe the influence of different process conditions, for example reaction temperature, pressure, conversion or selectivity, on the process according to the invention. They are compiled in table 1.

These simulations were carried out according to the calculations in example 1 for an annual capacity of methanol of 1 million tonnes t. In analogy to example 1, $CO_2$ was assumed to be the sole by-product.

The results of examples 1 to 8 show that the above-described process constitutes an economically very attractive process for preparing $C_1$-$C_4$ oxygenates, preferably methanol, by direct oxidation of the corresponding $C_1$-$C_4$ alkanes, which no longer has the disadvantages of the processes described in the prior art.

Compared to the prior art (both for methanol synthesis via the conventional two-stage synthesis gas route (ICI process) and for methane direct oxidation), the process according to the invention is notable for a simpler process concept and, associated with this, for significantly lower capital costs.

TABLE 1

Influence of different process parameters on the resulting product stream and the specific energy consumption (examples 2-8). Boundary conditions: annual methanol capacity: 1 million tonnes, $CO_2$ selectivity = 100%-methanol selectivity.

| Example | Temperature [° C.] | Pressure [bar] | Methane conversion [mol %] | Methanol selectivity [%] | Methane flow rate (B) [t/h] | Oxygen flow rate (C) [t/h] | Solvent flow rate [t/h] |
|---|---|---|---|---|---|---|---|
| 2 | 350 | 50 | 5 | 90 | 1394 | 90 | 1150 |
| 3 | 150 | 50 | 5 | 90 | 1394 | 90 | 1150 |
| 4 | 150 | 50 | 3 | 90 | 2324 | 90 | 1750 |
| 5 | 150 | 50 | 7 | 90 | 995 | 90 | 865 |
| 6 | 150 | 50 | 5 | 85 | 1480 | 107 | 1240 |

TABLE 1-continued

Influence of different process parameters on the resulting product stream and the specific
energy consumption (examples 2-8). Boundary conditions: annual methanol capacity:
1 million tonnes, $CO_2$ selectivity = 100%-methanol selectivity.

| 7 | 150 | 50 | 5 | 95 | 1320 | 76 | 1090 |
| 8 | 150 | 100 | 5 | 90 | 1394 | 90 | 1071 |

| Example | Stream to pipeline (stream E) [t/h] | $CO_2$ content in stream E [mol %] | Specific energy consumption | | |
|---|---|---|---|---|---|
| | | | Power consumption [MW] | Steam credit [t/h] | Cooling water consumption [1000 m³/h] |
| 2 | 1342 | 0.5 | 2.4 | 122.4 | 4.9 |
| 3 | 1342 | 0.5 | 2.4 | 122.4 | 4.9 |
| 4 | 2271 | 0.3 | 4.0 | −18.4 | 9.8 |
| 5 | 943 | 0.7 | 1.7 | 191.0 | 2.8 |
| 6 | 1434 | 0.8 | 2.6 | 196.8 | 5.6 |
| 7 | 1261 | 0.3 | 2.6 | 56.8 | 4.7 |
| 8 | 1340 | 0.5 | 7.4 | 108.5 | 4.3 |

The invention claimed is:

1. A process for preparing $C_1$-$C_4$-oxygenates from a reactant stream A which comprises a $C_1$-$C_4$-alkane or a mixture of $C_1$-$C_4$-alkanes, by
   a) branching off a substream B of the reactant stream A and allowing it to react in a reactor with oxygen or an oxygenous gas stream C, which converts a portion of the $C_1$-$C_4$-alkane or a portion of the mixture which comprises $C_1$-$C_4$-alkanes to $C_1$-$C_4$-oxygenates,
   b) removing at least 90 mol % of the $C_1$-$C_4$-oxygenates formed from the product stream D resulting from step a) to form a remaining low boiler stream E and a high boiler stream F which comprises the $C_1$ to $C_4$ oxygenates removed,
which comprises combining the low boiler stream E with the reactant stream A without further workup and without combination with the substream B downstream of the branching site of the substream B.

2. The process according to claim 1, wherein the selectivity of the reaction in step a) for $C_1$-$C_4$-oxygenates is at least 70%.

3. The process according to claim 1, wherein 0.1 up to 10 mol % of the $C_1$-$C_4$-alkane or 0.1 to 10 mol % of the mixture which comprises $C_1$-$C_4$-alkanes is converted in step a) to $C_1$-$C_4$-oxygenates.

4. The process according to claim 1, wherein the low boiler stream E comprises carbon dioxide in an amount in the range from 0 to 3% by volume, based on the low boiler stream E.

5. The process according to claim 1, wherein the low boiler stream E comprises water in an amount in the range from 0 to 6% by volume, based on the low boiler stream E.

6. The process according to claim 1, wherein the reaction in step a) takes place at a temperature in the range from 400 to 900° C.

7. The process according to claim 1, wherein the reaction in step a) takes place at a pressure in the range from 1 to 200 bar.

8. The process according to claim 1, wherein the reaction in step a) takes place in the presence of a heterogeneous catalyst.

9. The process according to claim 1, wherein the reactant stream E comprises methane, and the $C_1$-oxygenates formed are methanol and/or formaldehyde.

10. The process according to claim 1, wherein the reactant stream A is natural gas and the $C_1$-oxygenate formed is methanol.

11. The process according to claim 1, wherein the reactant stream A comprises propane and the propane oxygenate formed is acrolein and/or acrylic acid.

12. The process according to claim 1, wherein the product stream D comprises ethanol, acetaldehyde, or a mixture thereof, as the $C_2$-oxygenate.

13. The process according to claim 1, wherein the product stream D comprises n-butanol, n-butanal, isobutanol, maleic anhydride, or a mixture thereof, as the $C_4$-oxygenate.

14. The process according to claim 1, wherein the reaction in step a) takes place at a temperature in the range from 40 to 900° C.

15. The process according to claim 1, wherein the reaction in step a) takes place at a temperature in the range from 60 to 800° C.

16. The process according to claim 1, wherein the reaction in step a) takes place at a temperature in the range from 100 to 700° C.

17. The process according to claim 1, wherein the reaction in step a) takes place at a temperature in the range from 150 to 650° C.

* * * * *